(12) United States Patent
Kim et al.

(10) Patent No.: US 12,078,386 B2
(45) Date of Patent: Sep. 3, 2024

(54) AIR CONDITIONER

(71) Applicant: LG ELECTRONICS INC., Seoul (KR)

(72) Inventors: Hakjae Kim, Seoul (KR); Sunghyun Nam, Seoul (KR); Jongyun Lee, Seoul (KR); Moonseop Bak, Seoul (KR); Heechul Park, Seoul (KR); Heejin Lee, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 440 days.

(21) Appl. No.: 17/552,696

(22) Filed: Dec. 16, 2021

(65) Prior Publication Data
US 2022/0196267 A1 Jun. 23, 2022

(30) Foreign Application Priority Data
Dec. 18, 2020 (KR) ........................ 10-2020-0178695

(51) Int. Cl.
*F24F 8/22* (2021.01)
*A61L 9/20* (2006.01)
(Continued)

(52) U.S. Cl.
CPC .................. *F24F 8/22* (2021.01); *A61L 9/20* (2013.01); *F24F 1/0022* (2013.01);
(Continued)

(58) Field of Classification Search
CPC .......... F24F 8/22; F24F 1/0063; F24F 1/0022; F24F 13/08; A61L 9/20; A61L 2209/12; A61L 2209/16
See application file for complete search history.

(56) References Cited

U.S. PATENT DOCUMENTS 5,755,103 A 5/1998 Na et al.
2005/0287051 A1 12/2005 Yuen

FOREIGN PATENT DOCUMENTS

JP S63-82128 5/1988
JP S64-038532 2/1989
(Continued)

OTHER PUBLICATIONS

European Search Report dated May 11, 2022 issued in Application No. 21215624.4.
(Continued)

*Primary Examiner* — Nicole M Ippolito
*Assistant Examiner* — Hanway Chang
(74) *Attorney, Agent, or Firm* — KED & ASSOCAITES

(57) ABSTRACT

Air conditioner is provided that may include a case having an inlet and an outlet provided below the inlet, a heat exchanger configured to heat exchange external air introduced into the case through the inlet, a blower fan disposed below the heat exchanger and configured to be rotated by a rotational shaft formed in a lateral direction so as to send air inside the case from the inlet to the outlet, a lower guide that guides air, which is blown toward a lower side of the blower fan by the blower fan, to the outlet, an upper guide spaced apart from the lower guide to form a discharge passage with the lower guide, and a sterilization device disposed at one side of the lower guide and having a sterilization lamp configured to emit ultraviolet light toward the blower fan. A lower end of the sterilization lamp may be disposed lower than an upper surface of the lower guide.

20 Claims, 9 Drawing Sheets

(51) Int. Cl.
   *F24F 1/0022*     (2019.01)
   *F24F 1/0063*     (2019.01)
   *F24F 13/08*      (2006.01)

(52) U.S. Cl.
   CPC ............ *F24F 1/0063* (2019.02); *F24F 13/08* (2013.01); *A61L 2209/12* (2013.01); *A61L 2209/16* (2013.01)

(56) References Cited

FOREIGN PATENT DOCUMENTS

| | | |
|---|---|---|
| JP | H11-182883 | 7/1999 |
| JP | 2005-188871 | 7/2005 |
| JP | 2011-47590 | 3/2011 |
| JP | 2011-226717 | 11/2011 |
| KR | 10-2007-0047105 | 5/2007 |
| KR | 10-2007-0080387 | 8/2007 |
| KR | 10-1347119 | 1/2014 |
| KR | 10-2020-0102864 | 9/2020 |
| KR | 10-2020-0110993 | 9/2020 |
| KR | 10-2020-0131115 | 11/2020 |
| WO | WO 2020/189682 | 9/2020 |

OTHER PUBLICATIONS

Korean Office Action issued in Application No. 10-2020-0178695 dated Jul. 15, 2022.
Japanese Office Action issued in Application No. 2021-204840 dated Nov. 29, 2022.
International Search Report dated Apr. 14, 2022 issued in Application No. PCT/KR2021/019214.

68  52  54  56

AIR CONDITIONER

CROSS-REFERENCE TO RELATED APPLICATION(S)

This application claims priority under 35 U.S.C. § 119 to Korean Application No. 10-2020-0178695, filed in Korea on Dec. 18, 2020, whose entire disclosure is hereby incorporated by reference.

BACKGROUND

1. Field

An air conditioner, and more particularly, an air conditioner for sterilizing the inside of a case are disclosed herein.

2. Background

An air conditioner may include a compressor that compresses refrigerant, a condenser that condenses the compressed refrigerant, an expander that expands the condensed refrigerant, and an evaporator that evaporates the expanded refrigerant. The air conditioner is a device that may heat or cool indoor air by flowing refrigerant through the aforementioned components to control a temperature of the indoor air.

The air conditioner may include an indoor unit having a heat exchanger that performs heat exchange for indoor air, and an outdoor unit having a heat exchanger that performs heat exchange for outdoor air. The indoor unit may supply heated or cooled air to an indoor space using a blower fan disposed therein. If the blower fan is continuously operated, bacteria may grow and spread in the case due to dust introduced into the indoor unit or condensate water generated in a heat exchanger disposed on one side of the indoor unit.

Korean Patent Application Publication No. 10-2020-0102864, which is hereby incorporated by reference, discloses a sterilization module provided to sterilize the inside of the case to prevent bacterial propagation in the case. However, as the location of a lamp for sterilization is adjacent to the blower fan and light emitted from the lamp is transmitted to the blower fan through a separate reflector, a range and performance of the sterilization may be limited.

Korean Patent Application Publication No. 10-2020-0110993, which is hereby incorporated by reference, discloses a sterilization module provided to sterilize the inside of the case to prevent bacterial propagation in the case. However, in the structure of the sterilization module disclosed in the aforementioned related art, there may be a problem that dew forms at a lower end of the structure and disrupts the flow of air.

In addition, in a case in which ultraviolet light is emitted through a sterilization lamp, when the ultraviolet light emitted from the lamp is exposed to the outside through an outlet, it may cause harmful effects to human bodies.

BRIEF DESCRIPTION OF THE DRAWINGS

Embodiments will be described in detail with reference to the following drawings in which like reference numerals refer to like elements, and wherein.

DETAILED DESCRIPTION

Figure 1:
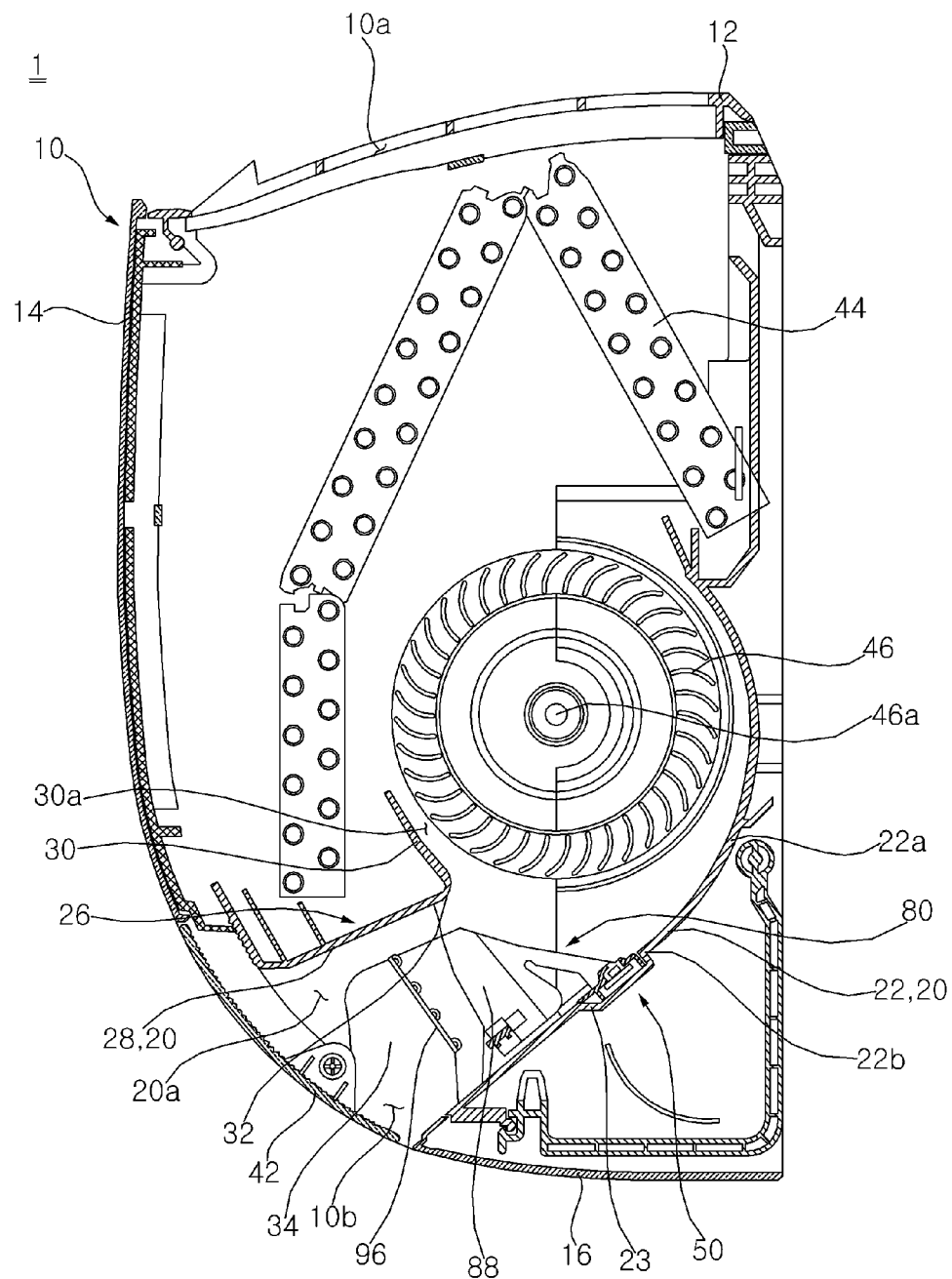
FIG. 1 is a cross-sectional view of an air conditioner according to an embodiment.

Advantages and features of embodiments and methods of achieving them will become apparent with reference to the embodiments described below in conjunction with the accompanying drawings. However, the embodiments are not limited to the embodiments disclosed below, but may be implemented in various different forms, and only these embodiments allow the disclosure to be complete, and common knowledge in the art to which the embodiments pertain. It is provided to fully inform those who have the scope, and the embodiments are only defined by the scope of the claims. Like reference numerals refer to like elements throughout.

Hereinafter, embodiments will be described with reference to the drawings for explaining an air conditioner according to the embodiments.

Referring to FIG. 1, air conditioner 1 may include a case 10 which forms an exterior of the air conditioner and has an inlet 10a and an outlet 10b formed therein, a heat exchanger 44 that heats or cools air flowing in the case 10, a blower fan 46 that causes air inside of the case 10 to flow to the outlet 10b, a discharge guide 20 that guides the air flowing by the blower fan 46 to the outlet 10b, and a sterilization device 50 disposed on or at one side of the discharge guide 20 and configured to emit ultraviolet light.

The case 10 may be formed with the inlet 10a through which air is suctioned in from an upper portion of an upper case 12 or a front case 14, and may be formed with the outlet 10b through which air is discharged from a lower portion of the front case 14. The case 10 may have a rectangular parallelepiped shape elongated from side to side, for example.

The air conditioner may be a wall-mounted air conditioner, and the outlet 10b may be formed below the inlet 10a so that the flow of air in the case 10 may flow from an upper side to a lower side. Referring to FIG. 1, the inlet 10a may be disposed higher than a center 46a of the blower fan 46, and the outlet 10b may be disposed lower than the center 46a of the blower fan 46.

An outer circumferential surface of the case 10 may include the upper case 12 having the inlet 10a formed therein; the front case 14 that extends downward from a front end of the upper case 12 and disposed to cover the front; a lower case 16 formed in an opposite direction of the upper case 12; and a side case (not shown) forming a surface perpendicular to the front case 14, the upper case 12, and the lower case 16.

Referring to FIG. 1, the front case 14 and the lower case 16 may be connected in a shape of a curved surface, and the outlet 10b may be formed in a portion at which the front case 14 and the lower case 16 are connected in the shape of the curved surface. The outlet 10b may be formed at a front lower side of the case 10.

A space in which the heat exchanger 44 and the blower fan 46 are disposed is formed in the case 10. A guide may be formed in the case 10 to guide air suctioned in through the inlet 10a to the blower fan 46 or to guide air blown by the blower fan 46 to the outlet 10b. The discharge guide 20 that guides the air blown by the blower fan 46 to the outlet 10b may be formed inside of the case 10.

The discharge guide 20 may form a discharge passage 20a through which the air flowing by the blower fan 46 flows. The discharge guide 20 guides the air flowing by the blower fan 46 to the outlet 10b. Referring to FIG. 1, the discharge passage 20a extends forward and downward from the blower fan 46.

Referring to FIG. 1, the discharge guide 20 may include an upper guide 28 disposed above the discharge passage 20a and a lower guide 22 disposed below the discharge passage 20a. The upper guide 28 may be connected to an upper end of the outlet 10b from a front portion based on the center 46a of the blower fan 46. The lower guide 22 may be connected to the lower end of the outlet 10b from a rear portion based on the center 46a of the blower fan 46.

The lower guide 22 may include a curved surface 22a formed as a curved surface to guide the air, which is discharged to a rear side of the blower fan 46 or a lower side of the blower fan 46 by the blower fan 46, to the outlet 10b, and a straight surface 22b that extends from the curved surface 22a to the outlet 10b to form a straight surface. A radius of curvature of the curved surface 22a may be larger than a radius of curvature of the blower fan 46. The curved surface 22a according to this embodiment may extend to a lower rear of the blower fan 46. Air blown by the blower fan 46 may be reflected by the curved surface 22a and flow toward the upper guide 28.

The straight surface 22b may naturally extend from the curved surface 22a. Accordingly, the straight surface 22b may extend at an inclination angle formed by an end of the curved surface 22a. The straight surface 22b may form a straight surface with an inclination angle so that the end faces downward in front.

A groove 23, in which a sterilization lamp 52 that emits ultraviolet light toward the blower fan 46 may be disposed, may be formed in the lower guide 22. The groove 23, in which a fixed body 82 of wind direction guide 80 may be mounted, may be formed in the lower guide 22. The groove 23 formed in the lower guide 22 may be disposed below the blower fan 46. The groove 23 formed in the lower guide 22 may be disposed at an upstream side based on an imaginary vertical line 46b that extends vertically from the center 46a of the blower fan 46.

The wind direction guide 80 may be mounted to the lower guide 22. The fixed body 82 of the wind direction guide 80 may be mounted on one side of the lower guide 22, and a motor 94 that changes a location of a moving body 90 of the wind direction guide 80 is disposed on the other side of the lower guide 22.

The upper guide 28 may form the discharge passage 20a with the lower guide 22, and be disposed to face the lower guide 22. The upper guide 28 may form a straight surface on an upstream side of the discharge passage 20a.

Referring to FIG. 1, the air conditioner 1 may include an inner frame 26 forming the upper guide 28 and disposed below the heat exchanger 44 to drain the condensed water falling from the heat exchanger 44. The inner frame 26 may include the upper guide 28, an upper end guide 30 bent at an upper end of the upper guide 28 and extending in a direction adjacent to the blower fan 46 to guide a portion of the air discharged from the blower fan 46 to the blower fan 46 again, and a connecting portion 32 that connects the upper end guide 30 and the upper guide 28.

The upper end guide 30 may extend along an outer circumferential surface of the blower fan 46 so as to be close to the center of the blower fan 46. The upper end guide 30 may be disposed as close to the blower fan 46 as possible to minimize an amount of air discharged from the blower fan 46 and flowing back to the blower fan 46.

The upper end guide 30 may form a backflow passage 30a through which a backflow of air flows between the blower fan 46 and the upper end guide 30. The connecting portion 32 may be gently bent so that a vortex generated between the discharge passage 20a and the backflow passage 30a may be minimized in the air discharged from the blower fan 46.

The inner frame 26 may include a supporter 36. The supporter 36 may include a first connector 38 to which a steel net 96 described hereinafter may be mounted, and a second connector 40 to which an outer vane 42 to be described below is rotatably connected.

The supporter 36 may be disposed between a pair of inner sidewalls 34 disposed at both ends of the upper guide 28. At least one supporter 36 may be disposed between the pair of inner sidewalls 34 disposed at both ends of the upper guide 28.

The first connector 38 may have a grille groove 38a in which a horizontal grille 96b of the steel net 96 is mounted. A plurality of grille grooves 38a spaced apart from each other in a vertical direction of the first connector 38 may be formed. An end groove (not shown) to which an end of the horizontal grille 96b of the steel net 96 may be mounted may also be formed in each of the inner side walls 34.

The second connector 40 may protrude toward the outlet 10b, and an outer vane 42 is rotatably disposed at an end of the second connector 40. The outer vane 42 may be disposed to be rotatable with respect to the case 10 to adjust a wind direction of air, which is discharged to the outlet 10b, in the vertical direction.

The sterilization device 50 may be disposed at or on the lower guide 22 to emit ultraviolet light toward the blower fan 46. The sterilization device 50 may be disposed toward the blower fan 46. The sterilization device 50 may be disposed on a surface formed by the lower guide 22 so as to minimize obstruction to the flow of air flowing along the lower guide 22.

The sterilization device 50 may include a sterilization lamp 52 that emits ultraviolet light toward a target, a printed circuit board 54 that applies power to or controls operation of the sterilization lamp 52, and a lamp cover 56 on which the sterilization lamp 52 and the printed circuit board 54 are fixedly disposed and mounted to the lower guide 22.

Figure 2:
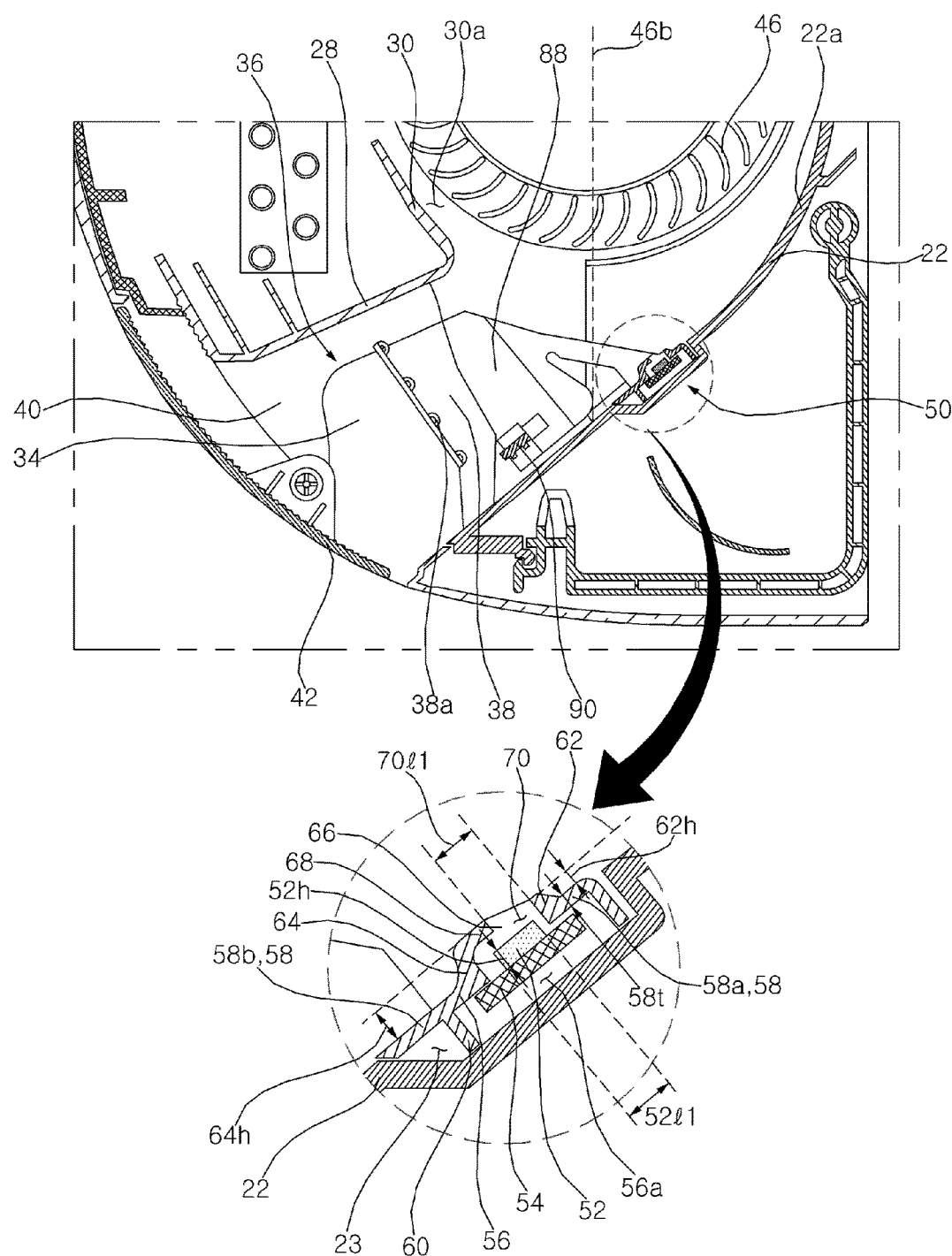
FIG. 2 is an enlarged cross-sectional view of an air conditioner for explaining a location of a sterilization device according to an embodiment.

The sterilization lamp 52 may emit light toward the blower fan disposed thereabove. Referring to FIG. 2, the sterilization lamp 52 may be disposed on a surface formed by the lower guide 22. That is, even in the groove 23, the sterilization lamp 52 may be disposed on an imaginary surface the upper surface of the lower guide 22 of which continues. The sterilization lamp 52 may be disposed in surface contact with an upper side of the printed circuit board 54. The printed circuit board 54 may be closely disposed from the lower side to the upper side of an upper wall 58 of the lamp cover 56 described hereinafter.

The lamp cover 56 may form an inclined surface a portion of which protrudes from the lower guide 22 and which is raised from upstream to downstream of the discharge passage 20a.

The lamp cover 56 may be inserted into the groove 23 formed in the lower guide 22. The lamp cover 56 may include a first space 56a in which the printed circuit board 54 is disposed, and a second space 56b in which the sterilization lamp is disposed above the first space 56a.

Referring to FIG. 2, the second space 56b may have a smaller area than that of the first space 56a. The lamp cover 56 may include the upper wall 58 formed in parallel with the surface formed by the lower guide 22, and an insertion wall 60 that extends downward from the upper wall 58 and disposed in the groove 23.

The upper wall 58 may be disposed in parallel with the straight surface 22b formed by the lower guide 22. Referring to FIG. 2, the upper wall 58 may include a first upper wall 58a disposed on or at an upstream side of the sterilization lamp 52, and a second upper wall 58b disposed on or at a downstream side of the sterilization lamp.

Referring to FIG. 2, a height 52h of the sterilization lamp 52 may be formed to have a size of 1 to 1.5 times a thickness 58t of the upper wall 58. As the height 52h of the sterilization lamp 52 is not significantly different from the thickness 58t of the upper wall 58, the lamp cover 56 covering the sterilization lamp 52 may form a low protruding height.

The lamp cover 56 may include a circumferential wall 62, 64, and 66 that extends upward from the upper wall 58 and forms the second space 56b in which the sterilization lamp 52 is disposed, and a top wall 68 disposed on or at upper sides of the circumferential wall 62, 64, and 66 and covering a portion of an upper side of the sterilization lamp 52.

Referring to FIG. 2, the circumferential wall 62, 64, 66 may include a first side wall 62 disposed on or at an upstream side of the sterilization lamp 52, second sidewall 64 disposed on or at a downstream side of the sterilization lamp 52, and a pair of third sidewalls 66 (see FIG. 5) that connects the first sidewall 62 and the second sidewall 64. The first side wall 62 may protrude upward from the first upper wall 58a in a heightwise direction of the sterilization device 50. The second side wall 64 may protrude upward from the second upper wall 58b in a heightwise direction of the sterilization device 50. In this case, with reference to FIG. 2, the heightwise direction of the sterilization device 50 is a direction in which the printed circuit board 54 and the sterilization lamp 52 are disposed, and a direction toward the sterilization lamp 52 may be set as the upper side and a direction toward the printed circuit board 54 may be set as the lower side.

The first sidewall 62 may be disposed on or at an upstream side of the sterilization lamp 52 to face air flowing along the lower guide 22. The second side wall 64 may be disposed on or at a downstream side of the sterilization lamp 52.

Figure 3:
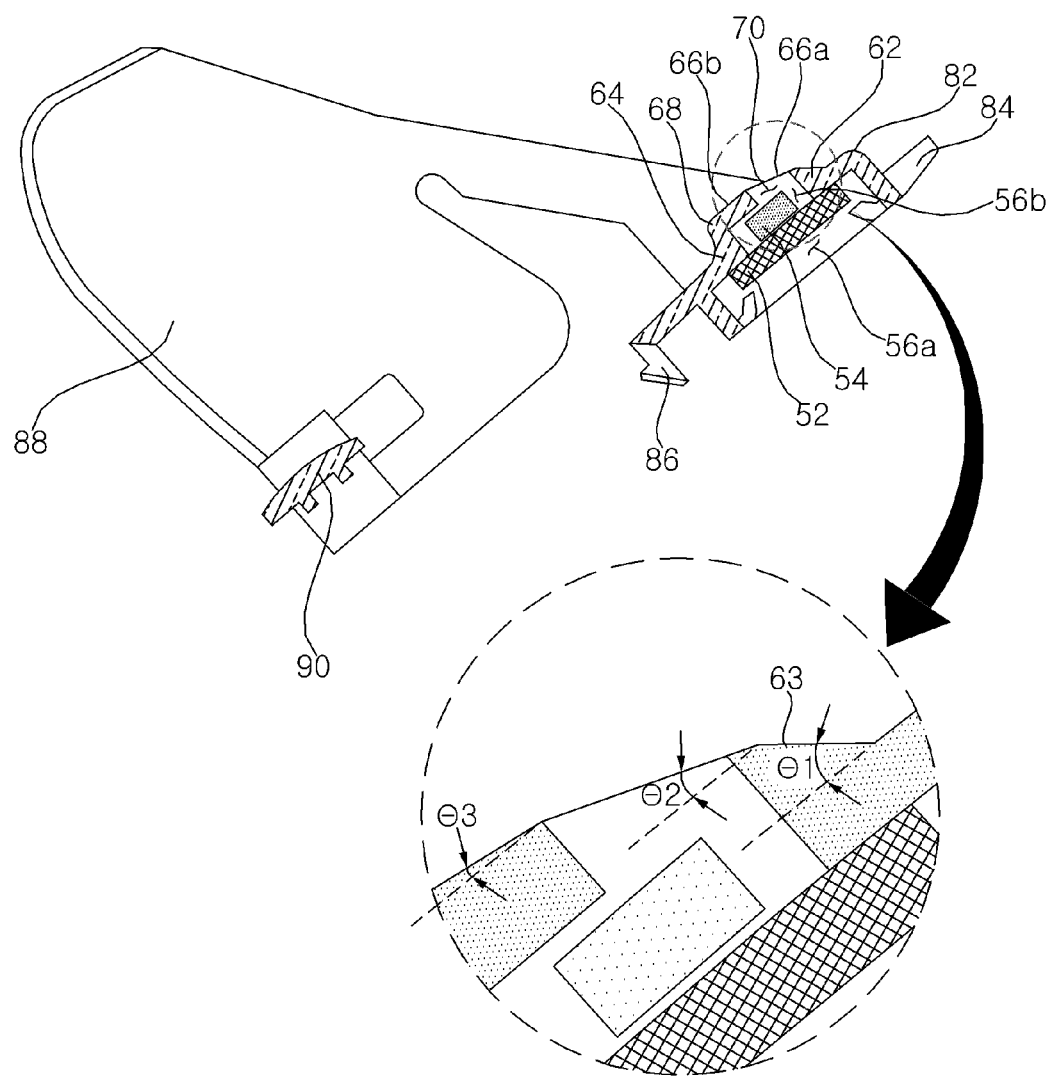
FIG. 3 is a cross-sectional view of a wind direction guide in which a sterilization device according to an embodiment is disposed.

Referring to FIG. 3, the first sidewall 62 may form an inclined surface 63 protruding from the upper wall 58 at an angle 81 from the upstream to the downstream. Referring to FIG. 3, the angle 81 formed between the inclined surface S1 and the upper wall 58 may be 45 degrees or less.

Referring to FIG. 2, the height 62h to which the first side wall 62 protrudes upward from the upper wall 58 in the heightwise direction of the sterilization lamp 52 may be 1 to 1.5 times the thickness 58t of the upper wall 58. The height 62h to which the first sidewall 62 protrudes upward from the upper wall 58 may be lower than a height 64h to which the second sidewall 64 protrudes upward from the upper wall 58.

Referring to FIG. 2, the height 64h to which the second sidewall 64 protrudes upward from the upper wall 58 in the heightwise direction of the sterilization device 50 may be 1 to 2 times the thickness 58t of the upper wall 58. The height 64h to which the second side wall 64 protrudes upward from the upper wall 58 in the heightwise direction of the sterilization device 50 may be greater than the height 62h to which the first side wall 62 protrudes upward from the upper wall 58 in the heightwise direction of the sterilization device 50.

Referring to FIG. 2, the pair of third sidewalls 66 may be connected to the first sidewall 62 at an upstream end and the second sidewall 64 at a downstream end. An upper end of the third side wall 66 may be formed such that a distance thereof from the upper wall 58 increases from the upstream to the downstream in the air flow direction. That is, the height of the third side wall 66 may increase from the upstream to the downstream in the air flow direction.

An upper end of the third side wall 66 may be divided into a first upper end 66a not connected to the top wall 68 and a second upper end 66b connected to the top wall 68. Referring to FIG. 3, an inclination angle 83 formed between the second upper end 66b and the upper wall 58 may be smaller than the inclination angle 82 formed between the first upper end 66a and the upper wall 58. Referring to FIG. 3, the inclination angle 82 formed between the first upper end 66a and the upper wall 58 may be smaller than the inclination angle 81 formed by the inclined surface 63 of the first side wall 62 relative to the upper wall 58.

The top wall 68 may cover a portion of the upper side of the sterilization lamp 52. The top wall 68 may cover a downstream region of the sterilization lamp 52 with reference to a center of the sterilization lamp 52. The top wall 68 may limit a transmission range of the sterilization lamp 52. The top wall 68 may prevent the ultraviolet light emitted from the sterilization lamp 52 from being emitted in a direction toward the outlet 10b.

An opening hole 70 through which the light emitted from the sterilization lamp 52 may be transmitted may be formed on the upstream side of the top wall 68. A length 70l1 of the opening hole 70 formed in an air flow direction may be shorter than a length 52l1 which the sterilization lamp 52 extends in a longitudinal direction of the sterilization device 50. In this case, the longitudinal direction of the sterilization device 50 may refer to a direction in which the straight surface 22b of the lower guide 22 extends. The opening hole 70 may be opened from an upstream end of the sterilization lamp 52 and may be opened up to a central region of the sterilization lamp 52.

Figure 8:
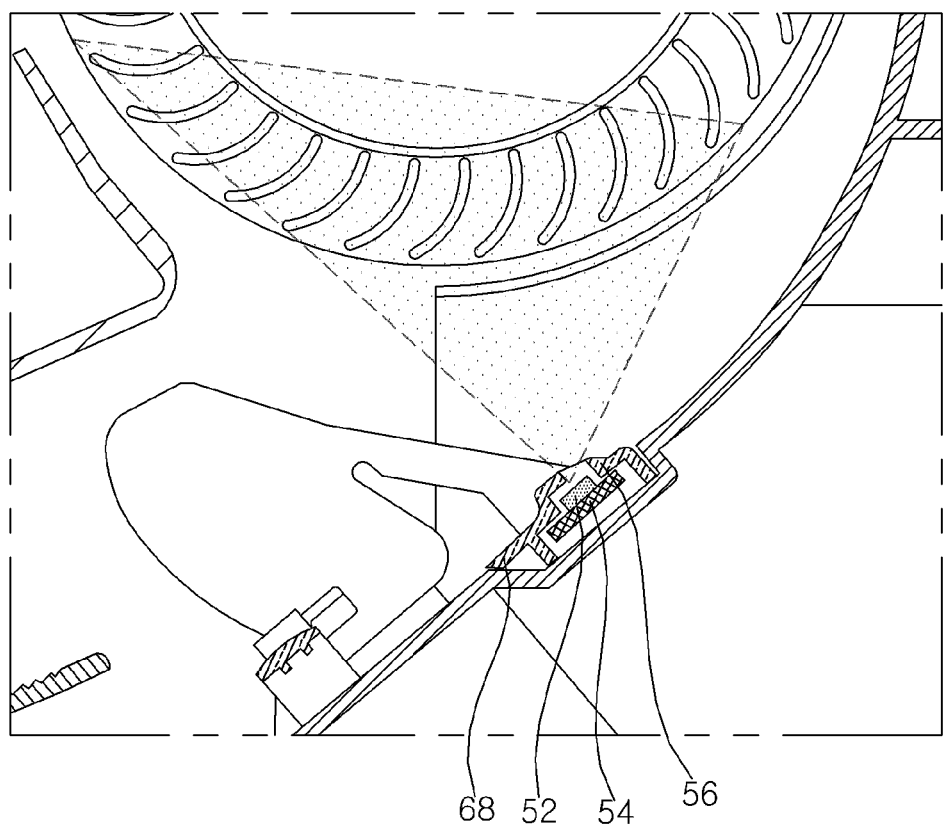
FIG. 8 is a view showing a transmission range of the sterilization device according to an embodiment.
Figure 9:
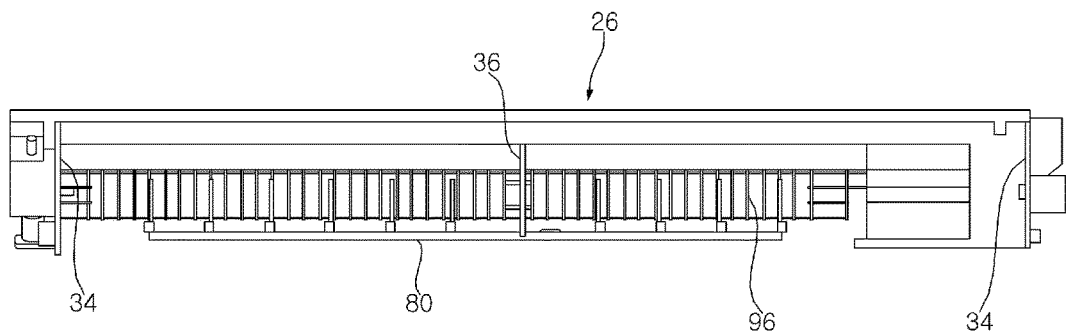
FIG. 9 is a view for explaining a location of a steel net and an inner frame according to an embodiment.
Figure 10:
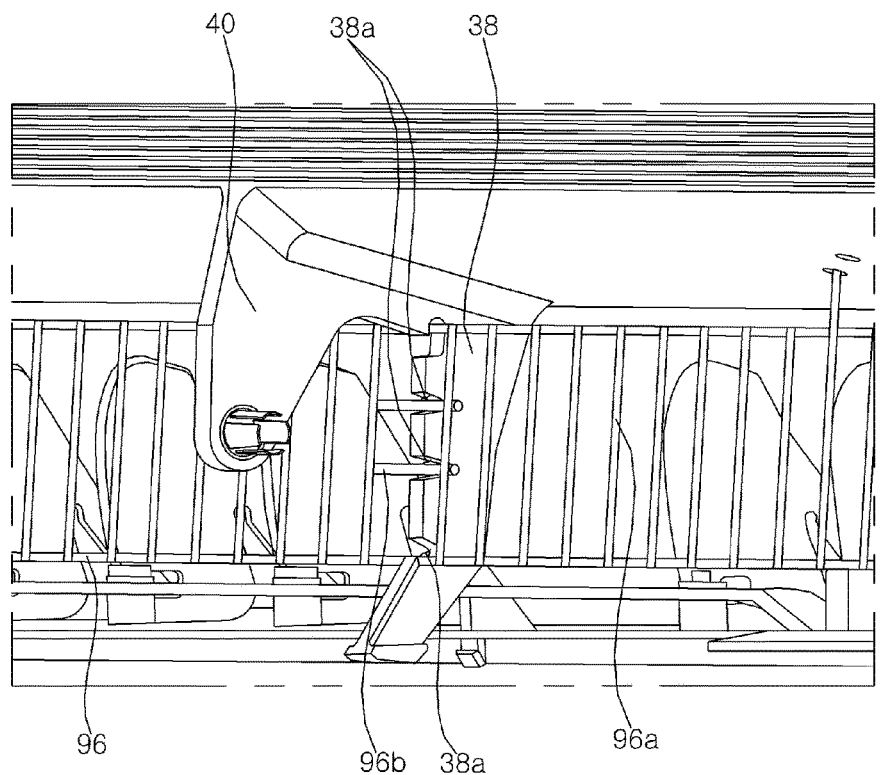
FIG. 10 is a view for explaining a steel net is mounted on a supporter according to an embodiment.

Referring to FIG. 8, the ultraviolet light generated by the sterilization lamp 52 may be emitted in a range in a front-rearward direction of the blower fan 46. In addition, since the transmission range is limited by the top wall 68, the ultraviolet light does not reach in a direction in which the upper guide 28 is disposed. In addition, as the sterilization lamp 52 almost does not protrude or protrudes very little from the lower guide 22, an area in which the lamp cover 56 disposed above the lower guide 22 protrudes upward of the lower guide 22 may be minimized. As a result, obstruction of the air flowing along the lower guide 22 may be minimized, and accordingly, it is possible to minimize generation of condensed water generated in a flow passage through which heat-exchanged air flows.

Figure 4:
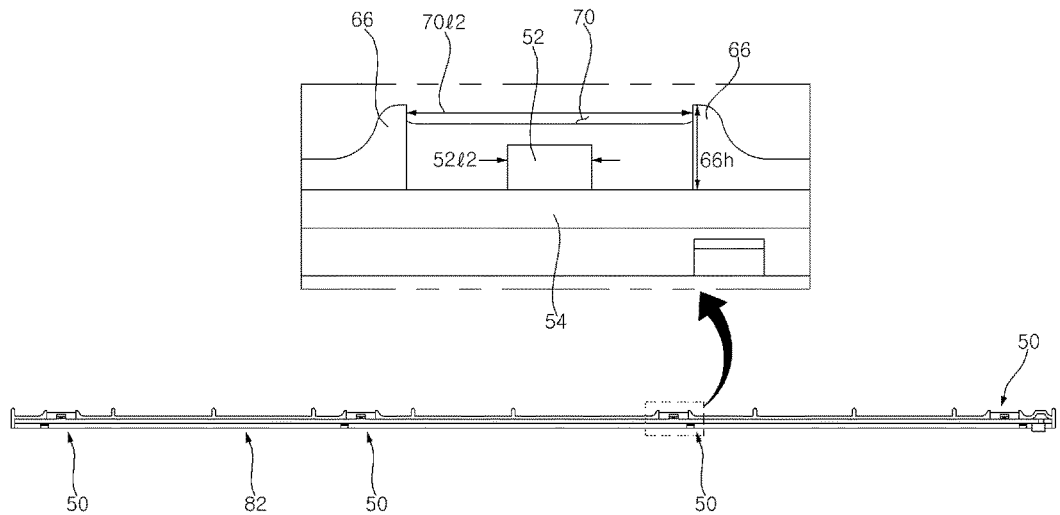
FIG. 4 is a cross-sectional view of one side of a fixed body of a wind direction guide in which a sterilization device according to an embodiment is disposed.
Figure 7:
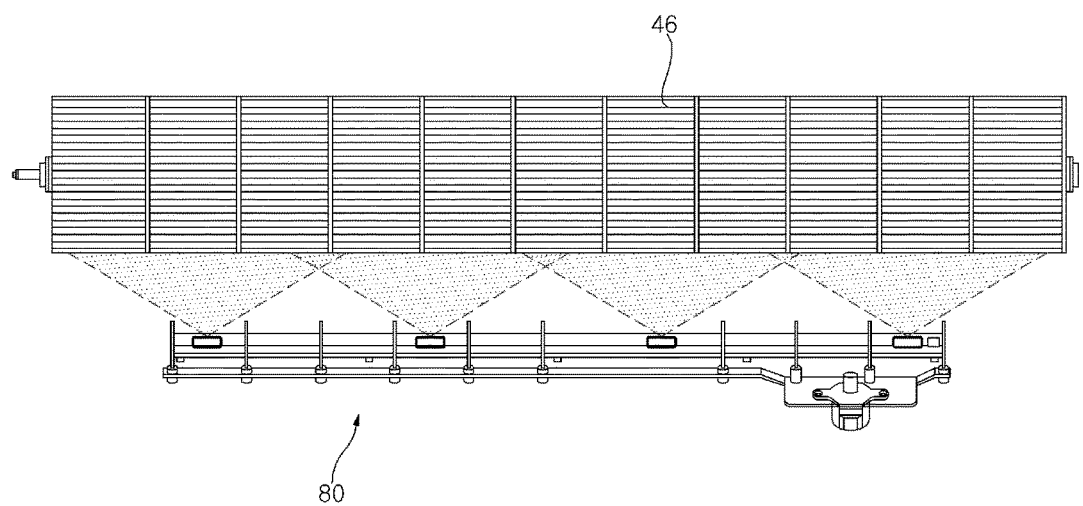
FIG. 7 is a view showing a location of a wind direction guide and a blower fan, and a transmission range of a sterilization lamp according to an embodiment.

Referring to FIG. 4, a length 7012 in which the opening hole 70 is opened in a direction perpendicular to the flow direction of air may be 3 times longer than a length 5212 by which the sterilization lamp 52 is formed in the widthwise direction, that is, in a lateral direction of the sterilization device 50. Therefore, as shown in FIG. 7, even if the range of the sterilization device 50 disposed at the wind direction guide 80 is smaller than the length to which the blower fan 46 is formed in the lateral direction, it is possible to emit ultraviolet light in a range of the lateral direction of the blower fan 46.

Referring to FIG. 4, in a portion where the opening hole 70 is formed, a height 66*h* of the third sidewall 66 may be 1.5 to 3 times the height 52*h* of the sterilization lamp 52.

The wind direction guide 80 may be mounted to the lower guide 22 to adjust a wind direction of air flowing through the discharge passage 20*a*. The wind direction guide 80 may adjust the wind direction of the air discharged to the outlet 10*b* in the lateral direction.

Figure 5:
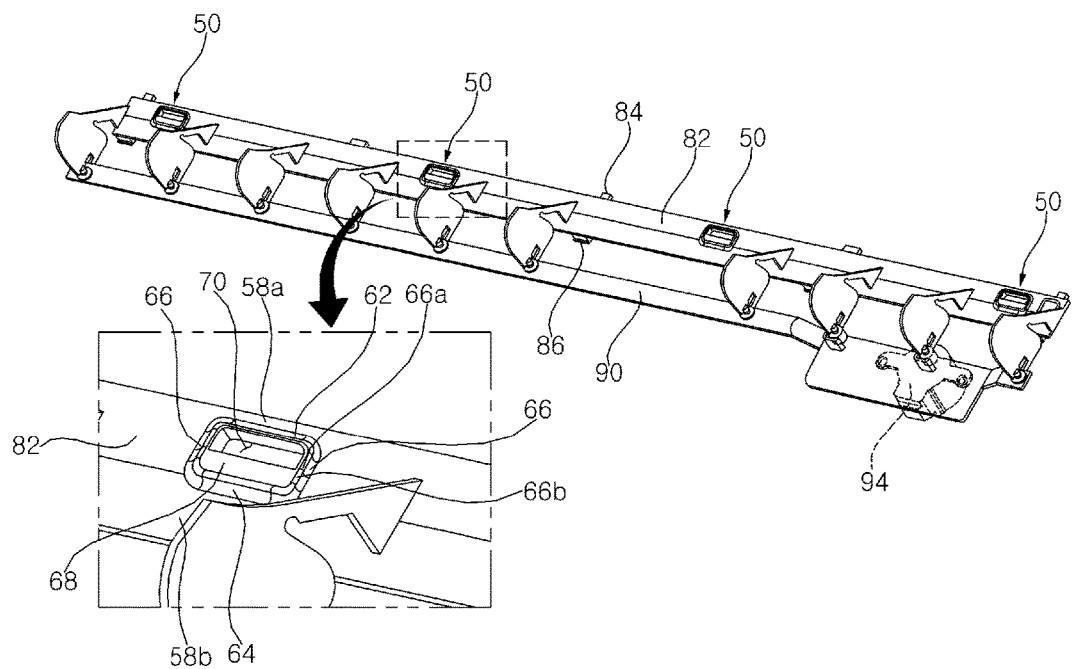
FIG. 5 is a perspective view of a wind direction guide, as viewed from a first side, according to an embodiment.
Figure 6:
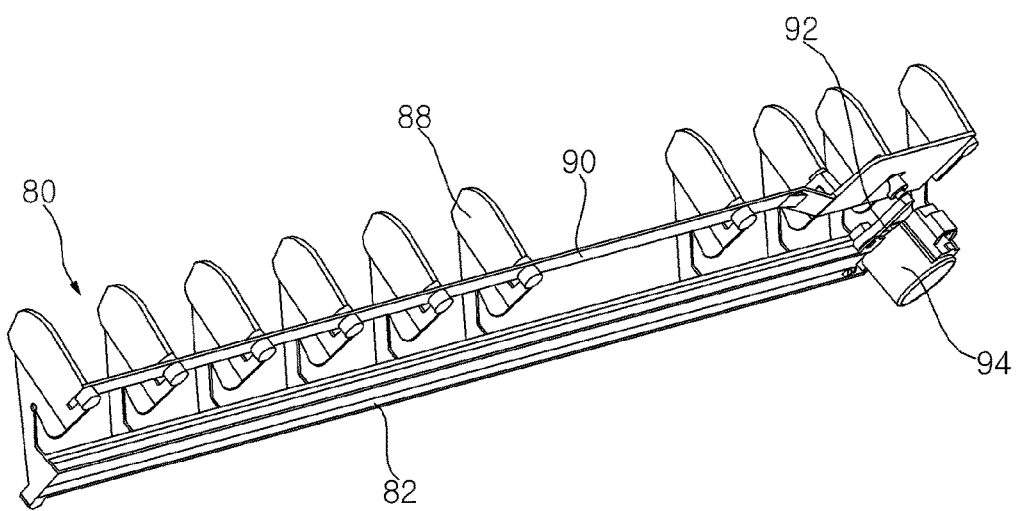
FIG. 6 is a perspective view of a wind direction guide, as viewed from a second side, according to an embodiment.

Referring to FIG. 5, a plurality of sterilization devices 50 may be disposed at or on the wind direction guide 80. The plurality of sterilization devices 50 may be spaced apart from each other in the lateral direction perpendicular to the flow direction of the air.

Referring to FIG. 5, the wind direction guide 80 may include a plurality of inner vanes 88 each disposed perpendicular to the upper guide 28 and the lower guide 22 in the discharge passage 20*a* with a downstream end that is movable in the lateral direction; the fixed body 82 mounted to the lower guide 22 to fix an upstream end of each of the plurality of inner vanes 88; the moving body 90 connected to a downstream end of each of the plurality of inner vanes 88 and controlling a location of each of the plurality of inner vanes 88; a motor 94 that moves the moving body 90 in the lateral direction; and a link 92 connecting the motor 94 and the moving body 90.

The fixed body 82 may be mounted to the groove 23 formed in the lower guide 22. The sterilization device 50 may be disposed in or on the fixed body 82. Referring to FIG. 5, a plurality of sterilization devices 50 may be spaced apart from each other in the lateral direction in the fixed body 82.

Referring to FIG. 5, an upper surface of the fixed body 82 may have a structure in which the upper surface naturally connects with the upper wall 58 of the lamp cover 56. The fixed body 82 and the lamp cover 56 of the sterilization device 50 may be integrally formed.

A fixing protrusion 84 to fix the fixed body 82 to the groove 23 of the lower guide 22, and a fixing hook 86 may be disposed at or on the fixed body 82. The fixing protrusion 84 may be disposed on one or a first side of the fixed body 82, and the fixing hook 86 may be disposed on a second opposite side of the fixed body 82.

The moving body 90 may be connected to each of the plurality of inner vanes 88 at a lower side of a downstream end of each of the plurality of inner vanes 88. A location of the moving body 90 may be changed by the link 92 which is rotated by the motor 94. Accordingly, the moving body 90 may change the location of the downstream end of each of the plurality of inner vanes 88.

The air conditioner 1 according to embodiments disclosed herein may include the steel net 96 that prevents a user's body from approaching an area to which ultraviolet light is emitted by the sterilization device 50. The steel net 96 may be disposed on or at a downstream side of the plurality of inner vanes 88 in the discharge passage 20*a*.

The steel net 96 may be mounted on the inner frame 26 so as to be disposed at the discharge passage 20*a*. The steel net 96 may include a plurality of vertical grilles 96*a*. The plurality of vertical grilles 96*a* may be spaced apart from each other in the lateral direction.

The steel net 96 may include a plurality of horizontal grilles 96*b* that are vertically spaced apart from each other and mounted in a grille groove 38*a* formed in the first connector 38. The plurality of horizontal grilles 96*b* may be mounted in the plurality of grille grooves 38*a* formed in the first connector 38 to fix the location of the steel net 96. In addition, the plurality of horizontal grilles 96*b* may be disposed at both first and second lateral ends of the net grille 96 to be mounted to the inner side wall 34.

Referring to FIG. 1, the steel net 96 may be disposed on or at a downstream side of the plurality of inner vanes 88. The steel net 96 may be disposed at a location spaced apart by a predetermined interval from the upper end of the upper guide 28 in a direction toward the outlet 10*b*. As the ultraviolet light emitted from the sterilization lamp 52 is emitted to the upper side of the upper end of the upper guide 28, the ultraviolet light does not reach the area in which the steel net 96 is disposed.

Figure 11:
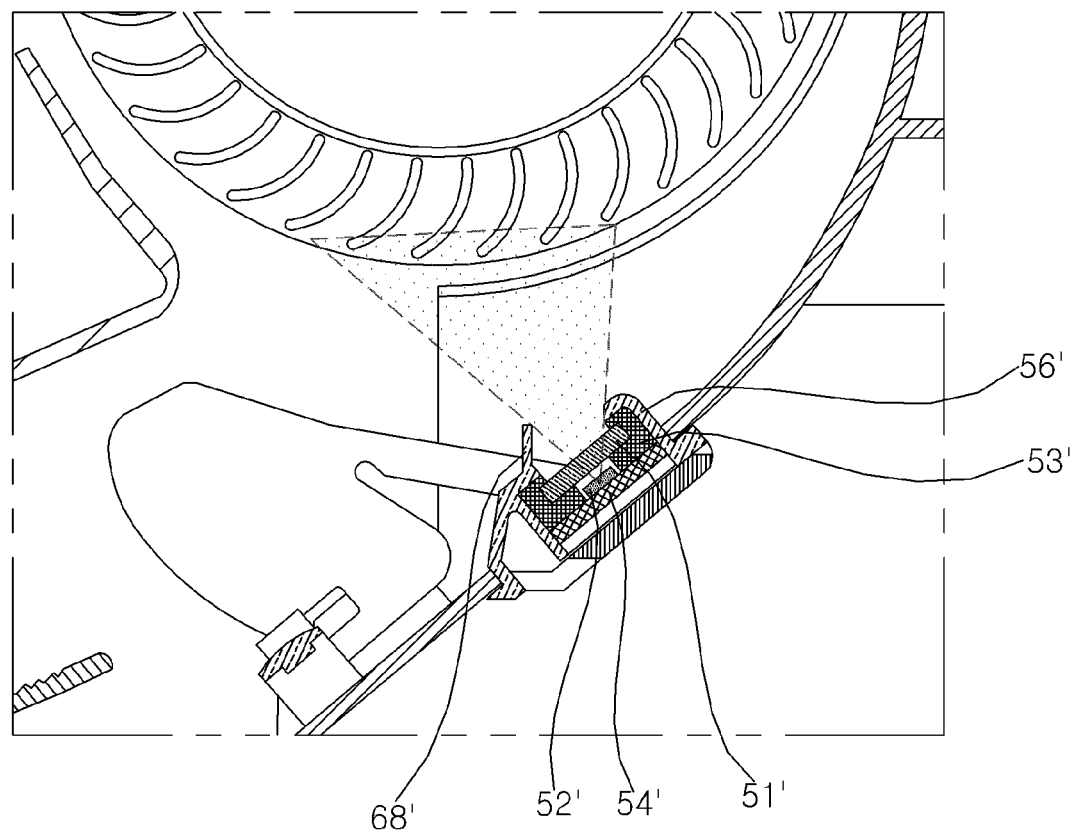
FIG. 11 is a cross-sectional view of an air conditioner including a sterilization device, as viewed from one side, according to another embodiment.

Referring to FIG. 11, a sterilization device 50' according to another embodiment will be described hereinafter. Differences from the previous embodiment described above will be mainly described.

The sterilization device 50' may include sterilizing lamp 52' that emits ultraviolet light toward a target, printed circuit board 54' that applies power to or controls operation of the sterilization lamp 52', lamp cover 56' on which the sterilization lamp 52' and the printed circuit board 54' are fixedly disposed and mounted to a lower guide 22, and a glass 51' disposed above the sterilization lamp 52' and covering an open area of the lamp cover 56'.

The sterilization device 50' may further include fixing member 53' that fixes the location of the glass 51' at a position spaced apart by a predetermined distance from the sterilization lamp 52'. The fixing member 53' may be disposed or at on an upper side of the printed circuit board 54' and may cover an upper side of the sterilization lamp 52'.

In the lamp cover 56', a top wall 68' that controls a transmission range of ultraviolet light emitted from the sterilization lamp 52' may be disposed on or at a downstream side where the opening hole is formed. Referring to FIG. 11, the top wall 68' may be formed to protrude upward from an upper wall of the lamp cover 56'. The top wall 68' may protrude toward an upstream side, limiting a transmission range of ultraviolet light.

Figure 12:
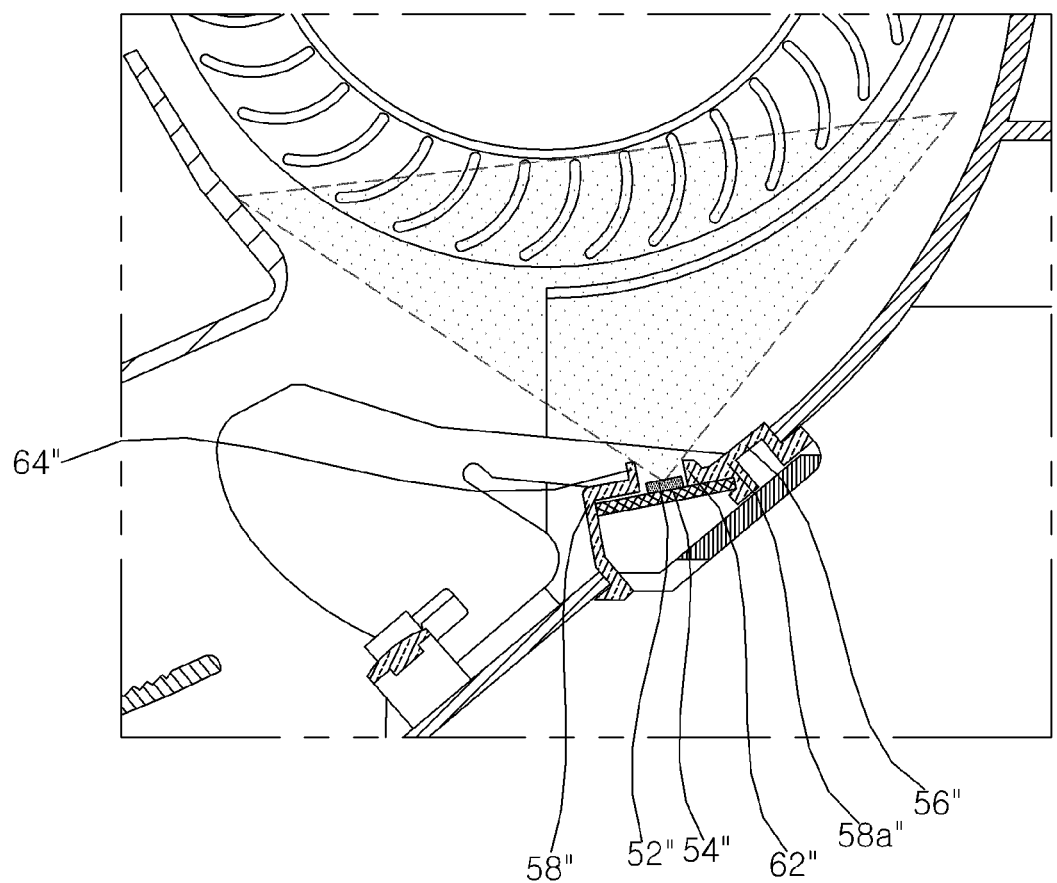
FIG. 12 is a cross-sectional view of an air conditioner including a sterilization device, as viewed from one side, according to yet another embodiment.

Referring to FIG. 12, a sterilization device 50" according to yet another embodiment will be described hereinafter. Differences from the previous embodiments will be mainly described.

The sterilization device 50" may include sterilizing lamp 52" that emits ultraviolet light toward a target, printed circuit board 54" that applies power to or controls operation of the sterilization lamp 52", and lamp cover 56" to which the sterilization lamp 52" and the printed circuit board 54" are fixedly disposed and mounted to a lower guide 22.

The lamp cover 56" may include a first upper wall 58*a"*, and a second upper wall 58*b"*, which is disposed on or at a downstream side of the first upper wall 58a" and in which an opening hole is formed. The first upper wall 58a" may form a surface parallel to the lower guide 22.

The second upper wall 58b" may be inclined relative to the first upper wall 58a". An inclination angle formed between the second upper wall 58b" and the first upper wall 58a" may be 45 degrees or less. The printed circuit board 54" may be disposed under the second upper wall 58b". An opening hole in which the sterilization lamp 52" may be disposed may be formed in the second upper wall 58b". At a portion at which the opening hole is formed in the second upper wall 58b", a first sidewall 62" disposed on or at an upstream side of the sterilization lamp 52" and a second sidewall 64" disposed on or at a downstream side of the sterilizing lamp 52" may be provided. A height of the second sidewall 64" may be greater than a height of the first sidewall 62".

The second sidewall 64" may protrude upward from the second upper wall 58b", thereby limiting a transmission range of ultraviolet light from the sterilization lamp 52".

Although embodiments have been shown and described, it will be appreciated by those skilled in the art that changes may be made to these exemplary embodiments without departing from the principles and spirit. Accordingly, the scope is not construed as being limited to the described exemplary embodiments, but is defined by the appended claims as well as equivalents thereto.

An air conditioner according to embodiments disclosed herein has at least one or more of the following advantages.

First, as a sterilization lamp is mounted in a groove formed in a lower guide and a lower end of the sterilization lamp is disposed lower than an upper surface of the lower guide, it is possible to minimize an area by which the sterilization device protrudes from the lower guide. This leads to an advantage in that it is possible to minimize flow resistance caused by a resistance body in air flowing along the lower guide. That is, there is an advantage of sterilizing a blower fan while maintaining stable air flow.

Second, as an area to which the ultraviolet light reaches is limited using a lamp cover, ultraviolet light is not exposed to the outside of the air conditioner. Thus, there is also an advantage of sterilizing the blower fan inside of the air conditioner, thereby preventing a safety issue.

Third, as a steel net is disposed in a discharge passage, it is possible to prevent a user from approaching the area to which the ultraviolet light is emitted. There is also an advantage of doubly preventing the user from being exposed to the ultraviolet light, thereby preventing a safety issue.

Embodiments disclosed herein provide an air conditioner in which a sterilization device does not obstruct flow of air blown by a blower fan. Embodiments disclosed herein also provide an air conditioner that sterilizes a blower fan that operates inside of the air conditioner and has a limited transmission range of ultraviolet light so that the ultraviolet light for sterilization cannot reach the outside of the air conditioner. Embodiments disclosed herein also provide an air conditioner capable of preventing a user's body, for example, from approaching an area to which ultraviolet light reaches in the air conditioner.

Embodiments disclosed herein are not limited to the above-described advantages, and other advantages, which are not described above, may be clearly understood by those skilled in the art through the specification.

Embodiments disclosed herein provide an air conditioner that may include a case in which an inlet and an outlet provided below the inlet are formed, a heat exchanger configured to exchange external air introduced into the case through the inlet, a blower fan disposed below the heat exchanger and rotating with respect to a rotational shaft formed in a left-right or lateral direction so as to blow air inside the case from the inlet to the outlet, a lower guide that guides air, which is flowing to a lower side of the blower fan due to the blower fan, to the outlet, an upper guide spaced apart from the lower guide to form a discharge passage with the lower guide, and a sterilization device disposed on or at one side of the lower guide and having a sterilization lamp configured to emit ultraviolet light toward the blower fan. A lower end of the sterilization lamp may be disposed lower than an upper surface of the lower guide.

The sterilization device may include the sterilization lamp, a printed circuit board configured to control operation of the sterilization lamp, and a lamp cover in which the sterilization lamp and the printed circuit board are fixedly disposed and mounted in a groove of the lower guide. In the lamp cover, a portion that protrudes from the lower guide may form an inclined surface which is raised from upstream to downstream of the discharge passage.

The lamp cover may include an upper wall formed parallel to a surface formed by the lower guide, and an insertion wall that extends downward from the upper wall and disposed in the groove. The printed circuit board may be closely disposed from a lower side to an upper side of the upper wall of the lamp cover, and the sterilization lamp may be disposed above the printed circuit board. A height of the sterilization lamp may be 1 to 1.5 times a thickness of the upper wall.

The lamp cover may include a circumferential wall that extends upward from the upper wall and forming a space in which the sterilization lamp is disposed, and a top wall disposed on an upper side of the circumferential wall and covering a portion of the upper side of the sterilization lamp. An opening hole through which the light emitted from the sterilization lamp is transmitted may be formed at an upstream side of the top wall.

The circumferential wall may include a first sidewall disposed on or at an upstream side of the sterilization lamp, a second sidewall disposed on or at a downstream side of the sterilization lamp, and a pair of third sidewalls that connects the first sidewall and the second sidewall. The first sidewall may include an inclined surface that protrudes from the upper wall from upstream to downstream. An angle formed by the inclined surface relative to a surface formed by the upper wall may be 45 degrees or less.

A height to which the first sidewall protrudes upward from the upper wall may be lower than a height to which the second sidewall protrudes upward from the upper wall. A height to which the second sidewall protrudes upward from the upper wall may be 1 to 2 times a thickness of the upper wall.

An upper end of the third side wall may be formed such that a distance thereof from the upper wall increases from upstream to downstream in the air flow direction. An upper end of the third side wall may be divided into a first upper end not connected to the top wall, and a second upper end connected to the top wall. An inclination angle formed by the second upper end relative to the upper wall may be smaller than an inclination angle formed by the first upper end relative to the upper wall. An inclination angle formed by the first upper end relative to the upper wall may be smaller than an inclination angle formed by the inclined surface of the first side wall relative to the upper wall.

The top wall may be disposed to cover an area downstream of the sterilization lamp with reference to a center of the sterilization lamp so as to limit a transmission range of the ultraviolet light emitted from the sterilization lamp. An opening hole through which the ultraviolet light emitted from the sterilization lamp is transmitted may be formed on an upstream side of the top wall. A length in which the opening hole may be formed in a flow direction of air may be shorter than a length in which the sterilization lamp extends in a longitudinal direction of the sterilization device.

The air conditioner may further include a wind direction guide mounted to the lower guide and controlling a wind direction of air flowing through the discharge passage. A plurality of sterilization devices spaced apart from each other in a left-right or lateral direction may be disposed in the wind direction guide.

The wind direction guide may include a plurality of inner vanes disposed perpendicular to the lower guide in the discharge passage and movably disposed in the left-right direction, a fixed body mounted to the lower guide to fix an upstream end of each of the plurality of inner vanes, a moving body connected with a downstream end of each of the plurality of inner vanes and controlling a location of each of the plurality of inner vanes, a motor configured to move the moving body in the left-right direction; and a link that connects the motor and the moving body. The sterilization device may be mounted to the fixed body. The fixed body may be mounted in a groove formed in the lower guide.

The air conditioner may further include a steel net having a plurality of grilles spaced apart from each other in a direction perpendicular to the discharge passage. The steel net may be disposed on or at a downstream side of the inner vane in the discharge passage. The steel net may be disposed at a location spaced apart from the upper end of the upper guide in a direction toward the outlet by a predetermined distance.

It will be understood that when an element or layer is referred to as being "on" another element or layer, the element or layer can be directly on another element or layer or intervening elements or layers. In contrast, when an element is referred to as being "directly on" another element or layer, there are no intervening elements or layers present. As used herein, the term "and/or" includes any and all combinations of one or more of the associated listed items.

It will be understood that, although the terms first, second, third, etc., may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section could be termed a second element, component, region, layer or section without departing from the teachings of the present invention.

Spatially relative terms, such as "lower", "upper" and the like, may be used herein for ease of description to describe the relationship of one element or feature to another element(s) or feature(s) as illustrated in the figures. It will be understood that the spatially relative terms are intended to encompass different orientations of the device in use or operation, in addition to the orientation depicted in the figures. For example, if the device in the figures is turned over, elements described as "lower" relative to other elements or features would then be oriented "upper" relative to the other elements or features. Thus, the exemplary term "lower" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Embodiments are described herein with reference to cross-section illustrations that are schematic illustrations of idealized embodiments (and intermediate structures). As such, variations from the shapes of the illustrations as a result, for example, of manufacturing techniques and/or tolerances, are to be expected. Thus, embodiments should not be construed as limited to the particular shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Any reference in this specification to "one embodiment," "an embodiment," "example embodiment," etc., means that a particular feature, structure, or characteristic described in connection with the embodiment is included in at least one embodiment. The appearances of such phrases in various places in the specification are not necessarily all referring to the same embodiment. Further, when a particular feature, structure, or characteristic is described in connection with any embodiment, it is submitted that it is within the purview of one skilled in the art to effect such feature, structure, or characteristic in connection with other ones of the embodiments.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. An air conditioner, comprising:
   a case having an inlet, and an outlet provided below the inlet;
   a heat exchanger configured to heat exchange external air introduced into the case through the inlet;
   a blower fan disposed below the heat exchanger and configured to be rotated by a rotational shaft that extends in a lateral direction so as to send air inside the case from the inlet to the outlet;
   a lower guide that guides air, which is blown by the blower fan toward to a lower side of the blower fan, to the outlet;

an upper guide spaced apart from the lower guide to form a discharge passage with the lower guide; and at least one sterilization device disposed at one side of the lower guide and having a sterilization lamp configured to emit ultraviolet light toward the blower fan, wherein a lower end of the sterilization lamp is disposed lower than an upper surface of the lower guide.

2. The air conditioner of claim 1, wherein the at least one sterilization device comprises:

the sterilization lamp;

a printed circuit board configured to control operation of the sterilization lamp; and a lamp cover configured to cover the sterilization lamp and the printed circuit board which are fixedly disposed and mounted in a groove of the lower guide, wherein the lamp cover includes a portion that protrudes from the lower guide in the form of an inclined surface that extends from an upstream side to a downstream side of the discharge passage in an air flow direction.

3. The air conditioner of claim 2, wherein the lamp cover further comprises an upper wall that extends parallel to a surface of the lower guide, and an insertion wall that extends downward from the upper wall and disposed in the groove, and wherein the printed circuit board is disposed adjacent to the upper wall of the lamp cover, and the sterilization lamp is disposed above the printed circuit board.

4. The air conditioner of claim 3, wherein a height of the sterilization lamp is 1 to 1.5 times a thickness of the upper wall.

5. The air conditioner of claim 3, wherein the lamp cover further comprises a circumferential wall that extends upward from the upper wall and forms a space in which the sterilization lamp is disposed, and a top wall disposed at an upper side of the circumferential wall and that covers a portion of the upper side of the sterilization lamp, and wherein an opening hole through which light emitted from the sterilization lamp is transmitted is formed at an upstream side of the top wall in the air flow direction.

6. The air conditioner of claim 5, wherein the circumferential wall comprises a first sidewall disposed at an upstream side of the sterilization lamp in the air flow direction, a second sidewall disposed at a downstream side of the sterilization lamp, and a pair of third sidewalls that connects the first sidewall and the second sidewall, and wherein the first sidewall comprises an inclined surface that protrudes from the upper wall from upstream to downstream.

7. The air conditioner of claim 6, wherein an angle formed by the inclined surface relative to a surface formed by the upper wall is 45 degrees or less.

8. The air conditioner of claim 6, wherein a height to which the first sidewall protrudes upward from the upper wall is lower than a height to which the second sidewall protrudes upward from the upper wall.

9. The air conditioner of claim 6, wherein a height to which the second sidewall protrudes upward from the upper wall is 1 to 2 times a thickness of the upper wall.

10. The air conditioner of claim 6, wherein an upper end of the third side wall is formed such that a distance thereof from the upper wall increases from the upstream side to the downstream side in the air flow direction.

11. The air conditioner of claim 6, wherein an upper end of the third side wall is divided into a first upper end not connected to the top wall and a second upper end connected to the top wall, and wherein an inclination angle formed by the second upper end relative to the upper wall is smaller than an inclination angle formed by the first upper end relative to the upper wall.

12. The air conditioner of claim 11, wherein the inclination angle formed by the first upper end relative to the upper wall is smaller than an inclination angle formed by the inclined surface of the first side wall relative to the upper wall.

13. The air conditioner of claim 5, wherein the top wall is configured to cover an area downstream of the sterilization lamp in the air flow direction with reference to a center of the sterilization lamp so as to limit a transmission range of the ultraviolet light emitted from the sterilization lamp.

14. The air conditioner of claim 5, wherein an opening hole through which the ultraviolet light emitted from the sterilization lamp is transmitted is formed on an upstream side of the top wall in the air flow direction, and wherein a length of the opening hole in the air flow direction is shorter than a length of the sterilization lamp in a longitudinal direction of the at least one sterilization device.

15. The air conditioner of claim 1, further comprising a wind direction guide mounted to the lower guide and controlling a wind direction of air flowing through the discharge passage, and wherein the at least one sterilization device comprises a plurality of sterilization devices spaced apart from each other in a lateral direction in the wind direction guide.

16. The air conditioner of claim 15, wherein the wind direction guide comprises:

a plurality of inner vanes disposed perpendicular to the lower guide in the discharge passage and movably disposed in the lateral direction;

a fixed body mounted to the lower guide to fix an upstream end of each of the plurality of inner vanes;

a moving body connected with a downstream end of each of the plurality of inner vanes and controlling a location of each of the plurality of inner vanes;

a motor configured to move the moving body in the lateral direction; and a link that connects the motor and the moving body, wherein the plurality of sterilization devices is mounted to the fixed body.

17. The air conditioner of claim 16, wherein the fixed body is mounted in a groove formed in the lower guide.

18. The air conditioner of claim 1, further comprising a steel net having a plurality of grilles spaced apart from each other in a direction perpendicular to the discharge passage, wherein the steel net is disposed at a downstream side in the air flow direction of the inner vane in the discharge passage.

19. The air conditioner of claim 18, wherein the steel net is disposed at a location spaced apart from the upper end of the upper guide in a direction toward the outlet by a predetermined distance.

20. An air conditioner, comprising:

a case having an inlet, and an outlet provided below the inlet;

a heat exchanger configured to heat exchange external air introduced into the case through the inlet;

a blower fan disposed below the heat exchanger and configured to create an air flow inside the case from the inlet to the outlet;

a discharge guide that guides air, which is blown by the blower fan toward to a lower side of the blower fan, to the outlet; and a plurality of sterilization devices spaced apart from each other in a lateral direction and disposed, respectively, in a plurality of grooves formed in the discharge guide, each having a sterilization lamp configured to emit ultraviolet light toward the blower fan and a lamp cover having an opening through which the ultraviolet light is directed toward the blower fan.

\* \* \* \* \*